United States Patent
Tuval et al.

(10) Patent No.: US 10,188,516 B2
(45) Date of Patent: Jan. 29, 2019

(54) STENT LOADING TOOL AND METHOD FOR USE THEREOF

(71) Applicant: Medtronic Ventor Technologies Ltd., Netanya (IL)

(72) Inventors: Yosi Tuval, Even Yehuda (IL); Yuri Sudin, Netanya (IL); Ido Kilemnik, Herzliya (IL); Igor Kovalsky, Minnetonka, MN (US); Raphael Benary, Tel Aviv (IL); Guy Ezekiel, Netanya (IL)

(73) Assignee: Medtronic Ventor Technologies Ltd., Netanya (IL)

( * ) Notice: Subject to any disclaimer, the term of this patent is extended or adjusted under 35 U.S.C. 154(b) by 260 days.

(21) Appl. No.: 15/183,208

(22) Filed: Jun. 15, 2016

(65) Prior Publication Data

US 2016/0361167 A1    Dec. 15, 2016

Related U.S. Application Data

(60) Continuation of application No. 14/192,614, filed on Feb. 27, 2014, now Pat. No. 9,393,112, which is a
(Continued)

(51) Int. Cl.
*A61F 2/24* (2006.01)
*A61F 2/00* (2006.01)
*A61F 2/95* (2013.01)

(52) U.S. Cl.
CPC .......... *A61F 2/2436* (2013.01); *A61F 2/0095* (2013.01); *A61F 2/2415* (2013.01);
(Continued)

(58) Field of Classification Search
CPC ............ A61F 2002/9522; A61F 2/0095; A61F 2/2427; A61F 2/2436
See application file for complete search history.

(56) References Cited

U.S. PATENT DOCUMENTS

| 3,334,629 A | 8/1967 | Cohn |
| 3,409,013 A | 11/1968 | Berry |

(Continued)

FOREIGN PATENT DOCUMENTS

| CN | 2007-100074433 | 8/2007 |
| DE | 3640745 | 6/1987 |

(Continued)

*Primary Examiner* — Gregory Anderson
(74) *Attorney, Agent, or Firm* — Medler Ferro Woodhouse & Mills PLLC

(57) ABSTRACT

A loading tool for withdrawing, crimping, and loading a stent-mounted valve into a delivery catheter, and for pushing the stent-mounted valve from the delivery catheter into a native heart valve orifice. The loading tool comprises at least one connector adapted for being removably connected to the stent of the stent-mounted valve. A crimping tool having a generally converging shape is adapted for use with the loading tool. Following connection of the loading tool to the stent-mounted valve, the loading tool operates to allow the stent-mounted valve to be drawn through the crimping tool, and loaded, in, a crimped state, into a delivery catheter. Also disclosed is a kit of the of the various components for effecting the delivery of the stent-mounted valve and a method for withdrawing, crimping, and loading a stent-mounted valve from a storage container into a delivery catheter for the performance of a transcatheter valve implantation procedure.

18 Claims, 12 Drawing Sheets

Related U.S. Application Data division of application No. 11/841,004, filed on Aug. 20, 2007, now Pat. No. 8,747,458.

(52) U.S. Cl.
CPC .......... *A61F 2/2418* (2013.01); *A61F 2/2427* (2013.01); *A61F 2002/9522* (2013.01); *A61F 2220/0016* (2013.01); *A61F 2230/0054* (2013.01)

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Stecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,911,752 A | 6/1999 | Dustrude et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |

(56) References Cited

U.S. PATENT DOCUMENTS

| | | |
|---|---|---|
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,051,104 A | 4/2000 | Jang |
| 6,059,809 A | 5/2000 | Amor et al. |
| 6,110,201 A | 8/2000 | Quijano et al. |
| 6,123,723 A | 9/2000 | Konya et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,164,339 A | 12/2000 | Greenhalgh |
| 6,168,614 B1 | 1/2001 | Andersen et al. |
| 6,171,335 B1 | 1/2001 | Wheatley et al. |
| 6,192,944 B1 | 2/2001 | Greenhalgh |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,559,603 B2 | 5/2003 | Iwami |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,627,873 B2 | 9/2003 | Tchakarov et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sleevers |
| 7,011,681 B2 | 3/2006 | Vesely |
| 7,018,401 B1 | 3/2006 | Hyodoh et al. |
| 7,041,128 B2 | 5/2006 | Mcguckin, Jr. et al. |
| 7,044,966 B2 | 5/2006 | Svanjdze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,144,408 B2 | 12/2006 | Keegan et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |

(56) References Cited

U.S. PATENT DOCUMENTS

| | | |
|---|---|---|
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,806,919 B2 | 10/2010 | Bloom et al. |
| 8,052,750 B2 | 11/2011 | Tuval |
| 8,167,932 B2 | 5/2012 | Bourang et al. |
| 8,348,995 B2 | 1/2013 | Tuval |
| 8,348,996 B2 | 1/2013 | Tuval |
| 8,414,643 B2 | 4/2013 | Tuval |
| 8,876,895 B2 | 11/2014 | Tuval |
| 2001/0002445 A1 | 3/2001 | Vesely |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149476 A1 | 7/2003 | Damm et al. |
| 2003/0149475 A1 | 8/2003 | Hyodoh et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Laskinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0254636 A1 | 12/2004 | Flagle et al. |
| 2004/0260317 A1 | 12/2004 | Bloom et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |

(56) References Cited

U.S. PATENT DOCUMENTS

| | | |
|---|---|---|
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0162731 A1* | 7/2006 | Wondka ............ A61B 17/12022 128/207.14 |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271081 A1 | 11/2006 | Realyvasquez |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Barlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |

(56) References Cited

U.S. PATENT DOCUMENTS

| | | |
|---|---|---|
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |

\* cited by examiner

STENT LOADING TOOL AND METHOD FOR USE THEREOF

RELATED APPLICATIONS

This application is a Continuation of and claims the benefit of U.S. patent application Ser. No. 14/192,614 filed Feb. 27, 2014, now allowed, which is a Division of and claims the benefit of U.S. patent application Ser. No. 11/841,004 filed Aug. 20, 2007, now U.S. Pat. No. 8,747,458. The disclosures of which are herein incorporated by reference in their entirety.

FIELD OF THE INVENTION

The present invention of a device and methods generally relates to the field of cardiac medical technology. In particular, the device relates to a loading tool that may be used in crimping, loading, and delivery a stent-mounted valve or other expandable prosthetic device.

BACKGROUND OF THE INVENTION

Stents are bioprosthetic devices that are typically used for counteracting restenosis, or the repeated narrowing of a blood vessel. Stents may also be used, for example, as shown in U.S. Patent Application 2006/0149360 to Schwammenthal, et al, as a component of a stent-mounted heart valve with mounted leaflets. The stent mounted valve implant described there includes clamping fingers that secure its position at a native valve orifice of the heart.

Such an implant is delivered to its site in the heart using a catheter assembly. To pass through the catheter, the prosthetic valve must be collapsed to a smaller profile. However, since the stent-mounted prosthetic valve has leaflets of pericardium material, it cannot be delivered to the hospital or medical facility in a collapsed or compressed state. Rather, the step of collapsing the implant for passage through the delivery device must be carried out shortly before the implantation procedure. Consequently, the valve, in an open slate, is delivered to the user in a container and that container typically contains a sterile, preservative medium such as glutaraldehyde.

Thus, prior to the implantation procedure, the stent-mounted valve must first be manually removed from the storage medium package, collapsed (perhaps by crimping), and then loaded into the delivery catheter in that crimped state.

Several cautions are to be observed prior to and during the step of loading the stent-mounted prosthetic valve. Since the material making up the stent is easily deformed or damaged, the stent must be handled with great care. Secondly, the stent must be crimped or otherwise collapsed to the smaller profile so that it fits properly inside of the catheter delivery tube. The step of collapsing the stent is a delicate process and, if not performed properly, may cause delay the implantation procedure or may entail excessive handling of the stent or even damage to the valve. Removal of the stem from the glutaraldehyde liquid medium in the storage and delivery container by surgically-gloved surgical personnel may be awkward.

Specialized tools may be used to minimize the risks associated with preparing the stent-mounted valve for the step of implanting the prosthetic valve in the heart.

U.S. Patent Application No. 2004/0186563, to Lobbi, discloses a heart valve that is loaded into the delivery catheter using a specialized tool. The valve is crimped or collapsed to a smaller profile by pulling it through a conical-shaped region of the specialized tool. One or more filaments threaded through the valve to allow such pulling and consequent crimping of the valve. A drawback to this procedure is that the step of threading the filaments through the valve can be a tedious and time-consuming process. Also, since the filaments have no purpose after the crimping step, they must be removed from the implant prior to the delivery procedure. Removal of the filaments may cause damage to the valve and may even partially undo the crimping step.

U.S. Patent Application No. 2003/0225445 to Derus et al., describes a loading device having a conical-shaped region for facilitating the collapse of a stent. As with the Lobbi procedure, a filament or the like is used to pull the stent through the loading device to collapse it.

Other devices for transferring a stent from a storage container to a delivery tool are described in U.S. Pat. No. 6,090,035 to Campbell, U.S. Pat. No. 5,693,066 to Rupp et al., U.S. Pat. No. 6,123,720 to Anderson et al., and European Patents WO 98/22044 and WO 97/09946, both to Borghi.

None of these patents or patent applications show the device and procedures described further hereinbelow, nor do they satisfactorily solve the problems which have been described above relating to transfer of the valve from a storage device, in which the valve is in an expanded state, to the delivery tool, in which the valve is in a substantially compressed state.

There is thus a need for a tool that allows for transfer of the valve or other prosthetic device from the storage container to the catheter delivery tube, in a relatively simple manner that requires only minimal handling.

SUMMARY OF THE INVENTION

Accordingly, it is a broad object of the present invention to overcome the above-mentioned disadvantages and limitations of the prior art and provide a loading tool suitable for extracting a stent-mounted valve from its packaging, crimping that stent-mounted valve into a profile suitable for introduction into a catheter delivery tube, and loading that stent mounted valve into a catheter delivery tube in a simple and reliable manner.

The described loading and delivery tool may be configured to become a part of the delivery system once it is loaded into a catheter delivery tube. Specifically, the loading tool may join to and be considered to become a part of an inner shaft of the catheter delivery tube, and, together with the inner shaft of the catheter, cooperate to push the stent-mounted valve outward from the catheter delivery tube once the appropriate location in the heart is reached. This functionality is due to the structure (and consequent rigidity) of the loading tool. The filaments used in the crimping step of the procedures found in the Lobbi and Derus et al published applications must be removed prior to the transcatheter procedure. As noted above, the filaments serve no function during the actual implantation of the stent.

The described loading tool may be used for withdrawing, crimping, and loading a stent-mounted valve into a catheter delivery tube, and further for facilitating pushing of the stent-mounted valve from the catheter delivery tube into a native heart valve orifice.

The loading tool may be configured to connect to and to be controllably be disconnected from the stent component of the stent-mounted valve. In one such variation, the loading tool may comprise one or more connectors adapted for being removably connected to the stent of the stent-mounted valve.

The connector or connection section of the loading tool may, for instance, comprise one or more prongs. For instance, the loading tool may comprise three prongs. Where the connector comprises one or more prongs, each prong may be characterized as having a substantially rigid portion and having a less rigid hinge region. Alternatively, each prong arm may be configured so that it flexes along its length. In either case, the flexibility of the prong allows the loading tool to become part of the delivery system during the transcatheter valve placement procedure. The distal end of each prong is configured in such a way that it may be attached to the stem-mounted valve via the stent component. In turn, the stent may include sites, portions, or members to be positioned in such a way to cooperate with, and thereby be attached to, the connector or connecting section of the loading tool. In certain instances, where the design of the stent and the connector permits, the stent may have at least three connecting members positioned around its periphery for facilitating attachment to three cooperating prongs of the loading tool.

Where prongs are used as connectors to the stent, the prongs may have a variety of configurations meeting the goal of removable and controllable attachment to and separation from the stent. In one variation, each prong is formed with a radial outwardly facing notch at its distal end which cooperatively engages a conforming connector of the stent-mounted valve. In usage, the operator places the ends of the prongs over the end of the stent and compresses the prongs on the loading tool to move the notched tips of the prongs and to align each of them with a corresponding connector on the stent. The user then releases the prongs such that each individual prong becomes engaged, with a single stem connecting member.

The prongs may have notches or openings that face outwardly or that face towards the end of the tool. In each instance, suitable interfering members would be employed to allow controllable attachment of the stem to the loading tool and subsequent release of the stent from the loading tool.

The loading tool may be pre-mounted onto the stent-mounted valve and provided in packaging together with a crimping tool. The crimping tool may have a generally converging-shape allowing the user to compress the stent-mounted valve just prior to introduction into the delivery catheter by pulling it from the packaging. This combination may be provided as a kit, perhaps sterilized and perhaps including a preservative for the valve and perhaps including printed instructions for use. In other variations, the loading tool and crimping tool may be provided separately, i.e., not attached to the stent-mounted valve. However, in the latter variation, the components may also be provided as a kit perhaps with separate or integrated packaging.

The crimping tool may have a converging-shape with an open, wide end and a narrower opposing end. The step of pulling the stent-mounted valve through the converging-shape crimping tool with the loading tool causes the stent-mounted valve to become compressed, due to the decreasing diameter of the crimping tool.

Once compressed, the stent-mounted valve (perhaps after a washing step to remove preservative) may be loaded directly into the catheter delivery tube for delivery using the transcatheter procedure. The loading tool and sleet may be configured so that the loading tool also grasps the stent by switching from a larger diameter (or expanded state) to a compressed state a it is drawn through the crimping tool along with the stent-mounted valve.

The loading tool may then be attached to a control and delivery member, e.g., a inner shaft or a catheter delivery tube, and then both the loading tool and the stent-mounted valve are drawn into the catheter delivery tube. This loading tool design greatly increases the ease of transfer of the valve front the storage device to the catheter delivery tube. Also, with this loading tool, the valve is subjected to minimal handling during transfer into the catheter delivery tube, a feature which assures the integrity of the valve itself.

As noted above, in one variation of the described component prongs, each prong is provided with a notched end to engage a cooperative connecting member or site located on, e.g., around the lower periphery of, the stent. In this variation, the diameter of the open connector, is larger than the diameter of the open stent. As the prongs are slightly compressed during attachment to the stent, the opening or notch in the end of the prong envelops a complementary connection on the stent to create and retain the connection with the stent.

In another variation, at least a portion of each of the prongs is constructed of a wire form. Each of the distal ends of the prongs is configured to engage a corresponding opening, e.g., an eye-hole, in a cooperating connector located on the stent.

The loading tool may comprise one or more medically safe polymeric, metallic, or combination materials which preserve a high degree of integrity during the procedure. Suitable materials include metals or alloys such as many of the stainless steels, super-elastic alloys such as NITINOL, titanium and titanium alloys, cobalt chromium alloys, and the like. Suitable materials also include polymers such as many of the Nylons, polycarbonates, polyimides, polyketones (such as polyetheretherketone (PEEK), polyetherketoneketone (PEKK), polyetherketone (PEK), polyetherketoneetherketoneketone (PEKEKK), and polyetheretherketoneketone (PEEKK), and generally a polyaryletheretherketone), and the like. Suitable polymeric materials, whether thermosets or thermoplastic, may be filled with, e.g., glass fibers, carbon fibers, polymeric fibers, ceramic fibers, and the like. The materials should be selected to have an elasticity allowing the loading tool to operate as described here.

The method of loading the stent mounted valve on the loading tool includes, in one variation, slightly compressing the prongs of the loading tool, inserting the prongs within the bottom of the stent-mounted valve, aligning the prongs with the stent connecting members, releasing the prongs to allow outward movement towards the stent causing the stent to become fixed into place. In this manner, the stent-mounted valve becomes connected to the loading tool and may now be drawn through the converging-shape crimping tool.

Once the stent is crimped, the loading tool is then coupled to a component of the delivery catheter assembly. The stool mounted valve and the loading tool are then drawn into the interior of the catheter delivery tube, the converging-shape crimping tool is detached, and the stent-mounted valve and loading tool are retracted farther into the catheter delivery tube in final preparation for the transcatheter procedure.

When the stent-mounted valve is delivered during the transcatheter procedure to the native heart valve, pushing the delivery tool slightly forward within the catheter delivery tube, or holding the stent-mounted valve in place as the catheter delivery tube is moved backward, will cause the stent-mounted valve to be exposed as it is released from constriction of the catheter delivery tube. The stent-mounted valve will then self-expand into position in the native heart valve.

There is also described a system for loading a stent-mounted valve into a catheter delivery tube for performance of a transcatheter valve implantation procedure. The system may include a loading tool configured to be removably connected to the stent of a stent-mounted valve. The loading tool may be configured to be coupled to the inner shaft of a catheter delivery tube. The system may also comprise d crimping tool having a generally converging shape.

The loading tool may comprise a handle detachable from the loading tool after the crimping of the stent-mounted valve is accomplished but prior to attachment of the loading tool to the catheter. By removing the handle, the loading tool and the stent-mounted valve may then be retracted together into the catheter delivery tube.

The stent may be comprised of a wire assembly and formed with a plurality of connecting members for facilitating connection to the prongs of the loading tool. The connecting members may comprise a region of the stern (e.g., when the stent is a wire-based structure or a specific wire is added to a stent structure for the purpose of connecting to the loading tool) or may comprise members specifically provided to cooperatively attach to a prong. In one variation, the prongs each comprise a notch for facilitating connection to the connecting members or regions of the stent. In other variations, the prongs each comprise a hook-shaped member for facilitating connection to the stent There is also described a method for withdrawing a stent-mounted valve from a storage container, crimping the stent-mounted valve, and loading the crimped stent-mounted valve into a catheter delivery tube for the performance of a transcatheter valve implantation procedure. The method includes:

(a) providing a stent-mounted valve in a substantially open state inside of a storage container;

(b) providing a loading tool comprising at least one connector adapted for being removably connected to the stent-mounted valve, and further adapted for being coupled to a inner shaft of a catheter delivery tube;

(c) providing a generally converging-shape crimping tool;

(d) attaching the loading tool to the stent-mounted valve using the at least one connector;

(e) withdrawing the stent-mounted valve from the storage container using the loading tool;

(f) pulling the stent-mounted valve through the crimping tool using the loading tool such that the stent-mounted valve becomes crimped;

(g) coupling the loading tool to the inner shaft of the catheter delivery tube, and (h) retracting the stent-mounted valve and the loading tool into the catheter delivery tube.

Step (d) of the procedure may be performed by the stent-mounted valve manufacturer. That step may comprise a step of providing a stent-mounted valve, the connected loading tool, and the converging-shape crimping tool inside of a storage container.

The procedure may include an additional step of washing the stent-mounted valve to remove traces of the storage medium.

The stent-mounted valve and the loading tool may be configured to automatically disconnect or separate from each other upon release and expansion of the stent-mounted valve within a native heart valve orifice.

Although the described device is described with reference to a stent-mounted valve, the loading tool may be readily adapted for use with any bio-prosthetic device which is switched from a substantially open state to a substantially closed state in order to load into a catheter delivery tube.

The described loading tool need not be disconnected from the stent-mounted valve prior to delivery, as required by prior art tools and methods. Instead, the loading tool itself becomes part of the delivery system and facilitates the release of the stent-mounted valve out of the catheter delivery tube when the implantation site is reached.

Additional features and advantages of the described device will become apparent from the following drawings and description.

BRIEF DESCRIPTION OF THE DRAWINGS

For a better understanding of the invention with regard to the embodiments thereof, reference is made to the accompanying drawings, not to scale, in which like numerals designate corresponding elements or sections throughout, and in which.

DETAILED DESCRIPTION OF THE PREFERRED EMBODIMENTS

Figure 1:
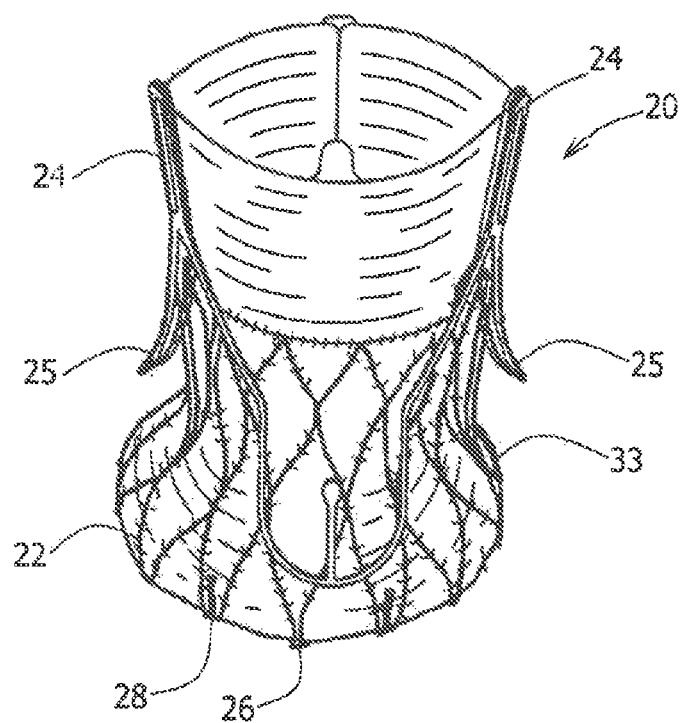
FIG. 1 is a perspective view of the stent-mounted valve, where the stent is a wire-based structure.

FIG. 1 is a perspective view of a self-expanding stent-mounted valve (20). Stent-mounted valve (20) may be of several types as is known to those skilled the art, but in the example of FIG. 1, the stem-mounted valve (20) is shown as a wire structure having a wire-mesh, expandable frame stent (22). Engagement arms (25) are typically configured to engage and/or rest against floors of aortic sinuses, to position the prosthetic valve assembly (20) in the native valve, and to apply an axial force directed towards the left ventricle. A more detailed description of our basic stent mounted valve is provided in U.S. patent application Ser. No. 11/024,908, filed Dec. 30, 2004, published as No. 2006/0149360, to Schwammenthal, et al., herein incorporated by reference in its entirety.

Figure 2:
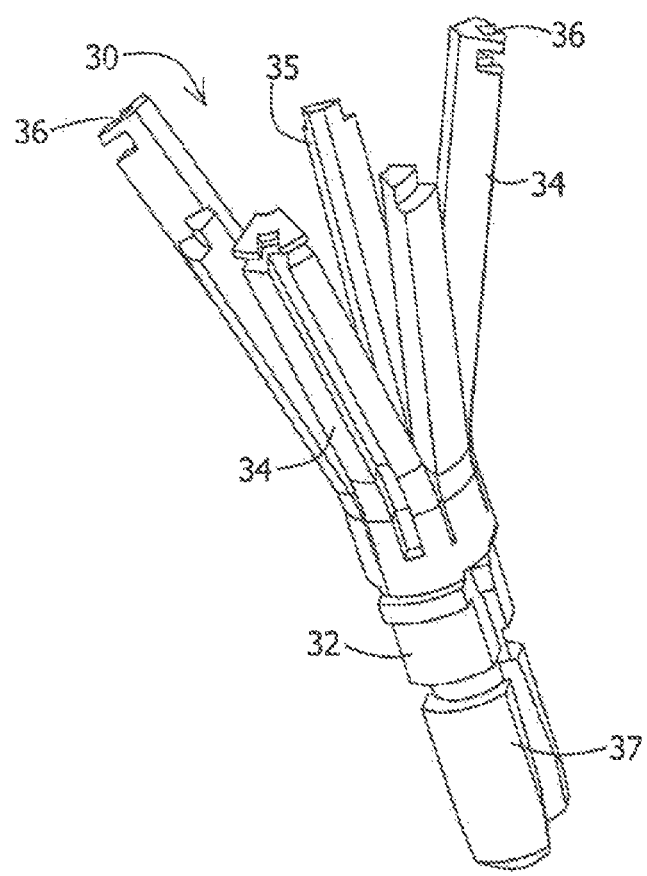
FIG. 2 is an enlarged, perspective view of a three-pronged loading tool in its natural, expanded state.
Figure 3:
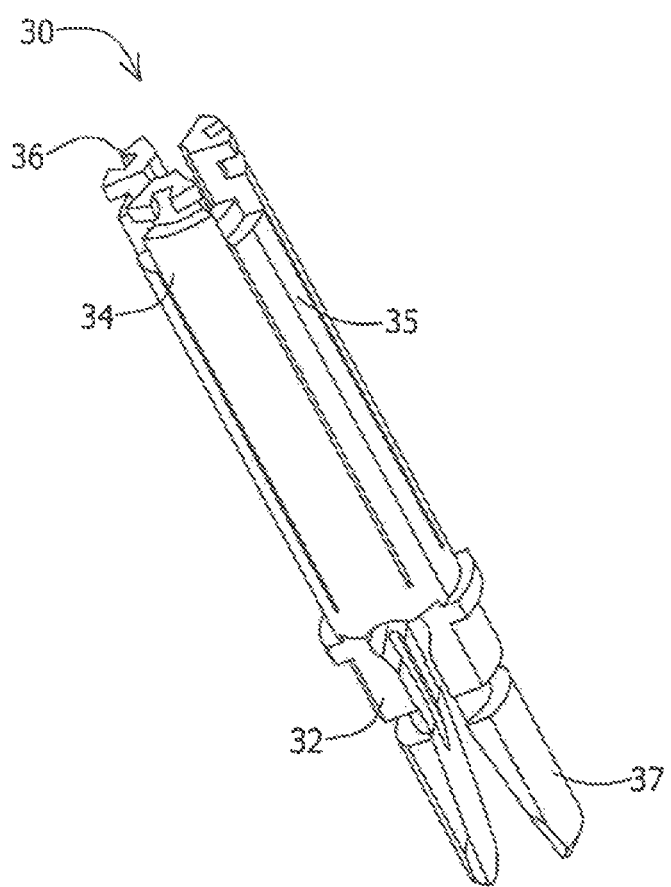
FIG. 3 is an enlarged view of a three-pronged loading tool, shown in its collapsed state.

FIGS. 2 and 3 provide enlarged views of a three-prong loading tool (30) in an open state and in a closed state, respectively. The loading tool (30) has a base (32) and three prongs (34), extending therefrom for facilitating connection to the stent-mounted valve using the notches (36) found at the prong tips. Three additional short prongs (35) extend from base (32) between prongs (34). Short prongs (35) serve to secure the positioning of loading tool (30) inside of a crimping tool, in a manner to be described further below. Base (32) is provided with a pusher connector or base connectors (37) for coupling to a catheter assembly component, e.g., an inner shaft.

It is appreciated that prongs (34) in this variation should be sufficiently flexible to allow the tips to be squeezed together (as shown in FIG. 3) and allow attachment to a stent-mounted valve. The prongs (34) may have a comparatively stiff section adjacent the prong tips and a comparatively more flexible section, a hinge-like area opposite the prong tips to allow the desired movement in attachment to the stent. Alternatively, the desired flexibility of the prongs (34) may be designed into the length of the prongs (34), i.e., each increment of a prong bends in a similar amount, thereby eliminating the hinge area of the earlier discussed variation. Other variations of prong flexibility, e.g., variation of the prong flexibility from a higher value at the tip to a lower flexibility at the base, are also suitable. Otherwise, prongs (34) should be sufficiently rigid to allow them to form a portion of the catheter delivery system.

In the variation illustrated, each prong (34) is provided with a radially outwardly facing notch (36) at its tip or distal end for connection to the stent of a stent-mounted valve such as those shown in FIG. 1. Loading tool (30) may be formed from suitable, elastic, medically safe polymeric, metallic, or combination materials which preserve a high degree of integrity during the procedure. Specifically, unless breakage or deformation is desired as a component of a particular design, the materials should not otherwise break or become deformed when in use. Suitable materials include metals or alloys such as many of the stainless steels, super-elastic alloys such as nitinol, titanium and titanium alloys, cobalt chromium alloys, and the like. Suitable materials also include polymers such as many of the Nylons, polycarbonates, polyimides, polyketones (such as polyetheretherketone (PEEK), polyetherketoneketone (PEKK), polyetherketone (PEK), polyetherketoneetherketoneketone (PEKEKK), and polyetheretherketoneketone (PEEKK), and generally a polyaryletheretherketone), and the like. Suitable polymeric materials, whether thermosets or thermoplastics, may be filled with, e.g., glass fibers, carbon fibers, polymeric fibers, ceramic fibers, and the like.

The design specifics of the loading tool (30) may be altered from those illustrated in the drawings for connecting to the stent (22), so long as the function of the tool is preserved. For instance, in the variation shown in FIGS. 2 and 3, the loading tool (32) includes prongs (34) with notches (36) that open outwardly, the prongs switching from an open state allowing attachment to the stent, to a closed state, allowing loading into the catheter delivery tube. With appropriate modification, the notches may, however, open inwardly or be open at the end of the prongs. However, a suitable loading tool is simply one having a connector or connector region permitting controllable connection to the stent, facilitating compression (or crimping) of the stent-mounted valve, loading of the stent-mounted valve into a catheter delivery tube, and controllably releasing the stent-supported valve at the delivery site.

As mentioned above, the depicted loading tool (30) includes three prongs (34). This number of prongs (34) may be chosen as a balance between providing adequate support of the stent during the crimping step and providing the minimum number of suitably functional mechanical components. Of course, this variation of the loading tool may include any other suitable number of prongs such as, but not limited to, two, four, five or six. In each case, the stent-mounted valve would typically be provided with a corresponding number of connecting members (or connecting regions) in the slant to allow cooperative connection therebetween. For example, in variations where the loading tool has three prongs, the stent generally would also have three prongs. However, the stent may be designed to include more than three connection members, sites, or regions to ease the step of connection between the loading tool and the sent by providing additional connection sites.

Figure 4:
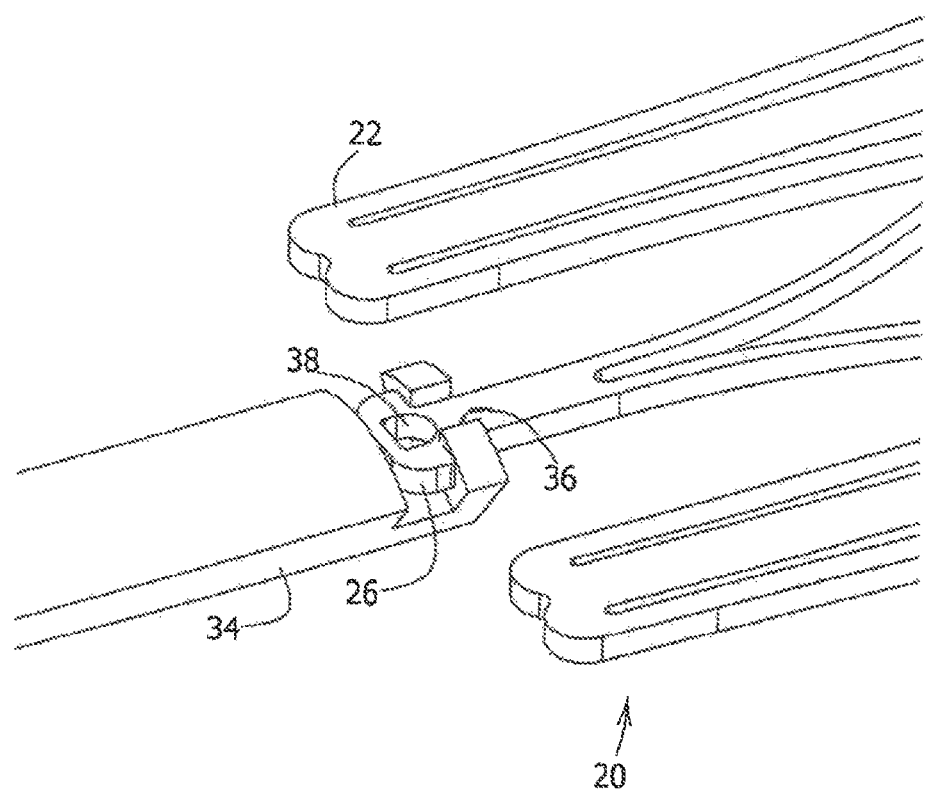
FIG. 4 is a close-up, detailed view showing attachment of the loading tool of FIGS. 2 and 3 to a self-expanding stent.

FIG. 4 is an enlarged, detailed view showing the connection of the loading tool of FIGS. 2 and 3 to a stent-mounted valve. Notch (36) of prong (34) connects to the stent connector (26) of stent (22) in the manner illustrated, with connector (26) seated inside of notch (36). The sleet connector (26) radially slides into notch (36). However, the notch (36) is configured so that the stem connector (26) does not substantially move axially in either direction. This configuration means that the connection is firm whether the loading tool is being used to pull the stent-mounted valve through the crimping tool or to push the crimped stent-mounted valve through the delivery catheter.

The loading tool (30) has a longitudinal axis and the at least one connector, in this case, comprising the prong(s) (34) is configured to removably attach to the stent (22) of the stent valve (20).

Figure 5:
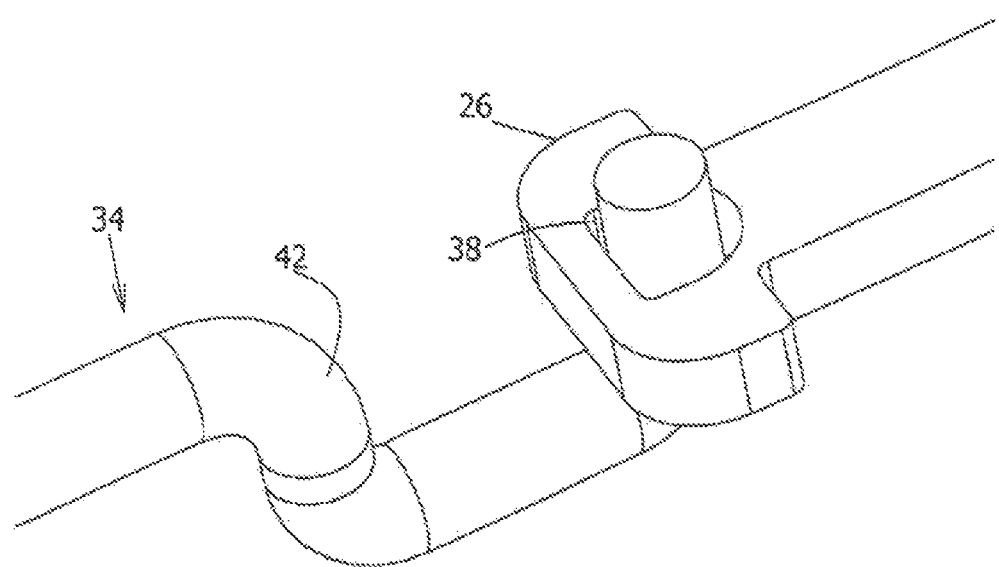
FIG. 5 is a close-up view of a portion of a self-expanding wire stent and a loading tool.

The depicted stent connector (26) includes an aperture (38) that is not necessary for the connection shown in FIG. 4, but may be used in conjunction with other prong variations, such as that shown in FIG. 5.

FIG. 5 is an enlarged, detailed view of an alternative connecting prong (34). In this variation, the prong (34) is provided with a hook member (42) at its distal end. The distal tip of the hook (42) passes through the aperture (38) in the stent connector (26). As is the case with prong variation discussed with regard to FIG. 3, the distal tip of the hook (42) prevents substantial, axial movement between the stent and the loading tool, but allows radial movement between the prong (34) and the stent valve during engagement and implantation of the valve.

The connection between the stent and the loading tool allows for the stent-mounted valve to be crimped and easily loaded into a catheter delivery tube, together with the loading tool. The depicted loading tools employ prongs having outward-facing notches. This means that the loading tool is placed inside the stent and the prongs grasp the stent from its interior. For those variations using a self-expanding stent, delivery of the stent-mounted valve allows the stent to undergo self-expansion. The stent expands away from the loading tool. This could be characterized as automatic disconnection of the stent from the loading tool.

Figure 6:
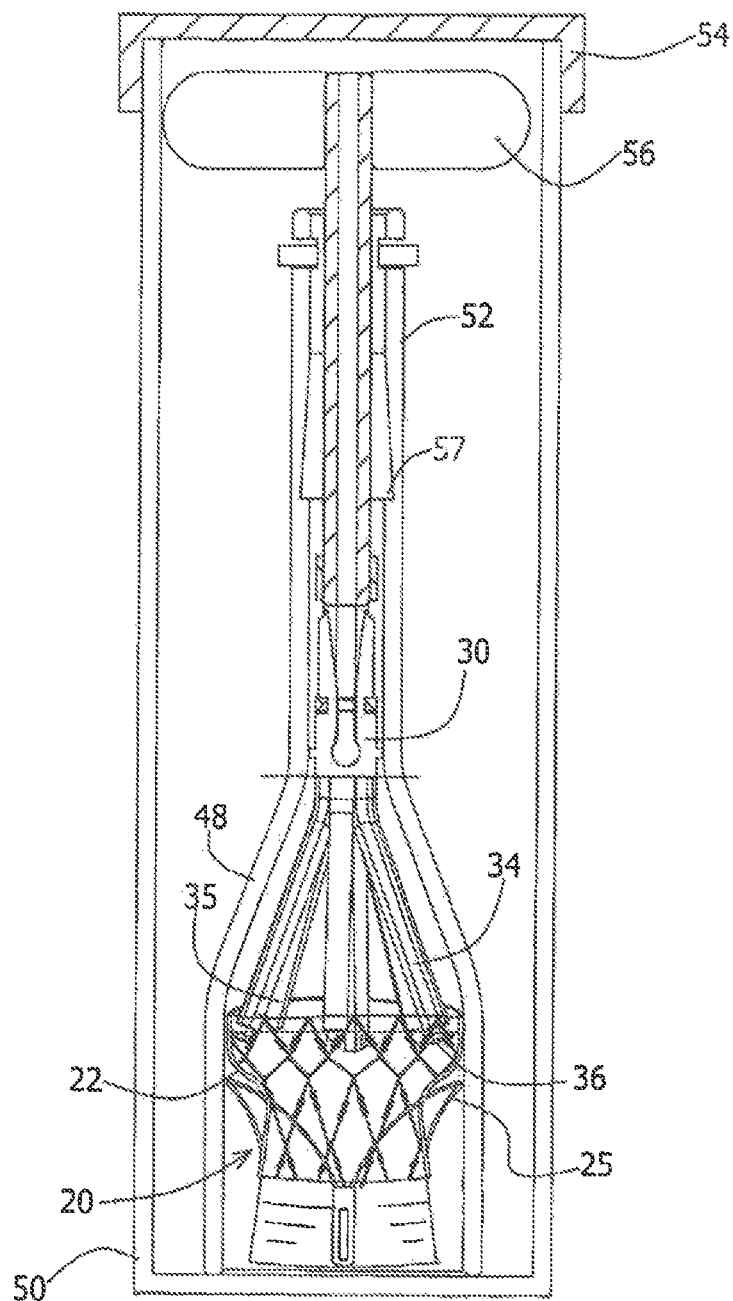
FIG. 6 is a schematic view, in partial cross-section, of a loading tool attached to a stent-mounted valve, a generally converging-shape crimping tool, in wide-mouthed bottle storage packaging.

FIG. 6 shows a partial cross-section of an assembly useful as a self-contained kit suitable for commercial delivery to a surgical user, e.g., a hospital, clinic, surgical suite, physician, etc. In addition to the assembly described below, additional exterior packaging and written instructions may be included as necessary or appropriate. In any case, the assembly comprises a loading tool (30) attached to (or attachable to) a stent-mounted valve (20). A generally converging-shape (or converging diameter) crimping tool (48) substantially surrounds the loading tool (30) and valve (20). These components are all included within a wide-mouthed bottle storage container (50) serving as packaging for the assembly. The crimping tool (48) may have any suitable hollow, generally converging shape that compresses the stent-mounted valve (20) as it moves through the interior of the crimping tool (48).

Stent-mounted valve (20) is shown as sitting at the bottom of bottle storage container (50). In the example illustrated, three-prong loading tool (30) is attached to stent (22) of stent-mounted valve (20) by a cooperative connection in which the stent connector (26) slides radially into notch (36) of prong (34) of loading tool (30), as shown in FIG. 4. Stent-mounted valve (20) and attached loading tool (30) are situated within converging-shape crimping tool (48). Bottle delivery or storage container (50) is filled with a sterile, non-volatile preservative, a fluid, commonly glutaraldehyde. The glutaraldehyde should be washed from the crimped components after their removal from the delivery and storage container (50).

After any exterior packaging and the top (54) are removed storage container (50), a user (even a user wearing sterile disposable gloves) can easily remove the components from the storage container (50) by gripping the crimping tool (48) and handle (56). The handle (56) is removably connected to loading tool (30). Pulling handle (56) with respect to the crimping tool (48) draws the stent-mounted valve (20) and loading tool (30) upwards through that converging-shape crimping tool (48). The action crimps stent-mounted valve (20) and compresses prongs (34, 35) of loading tool (30) as these components pass into and through the narrow neck (52) of converging-shape crimping tool (48).

Figure 7A:
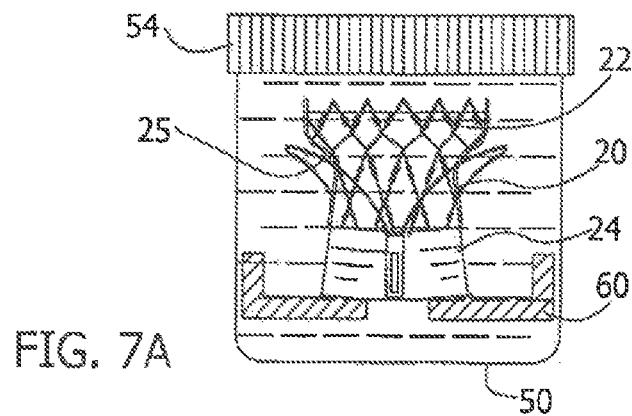
FIG. 7A is a partial cross-sectional view of a bottle storage packaging containing a stent-mounted valve.
Figure 7B:
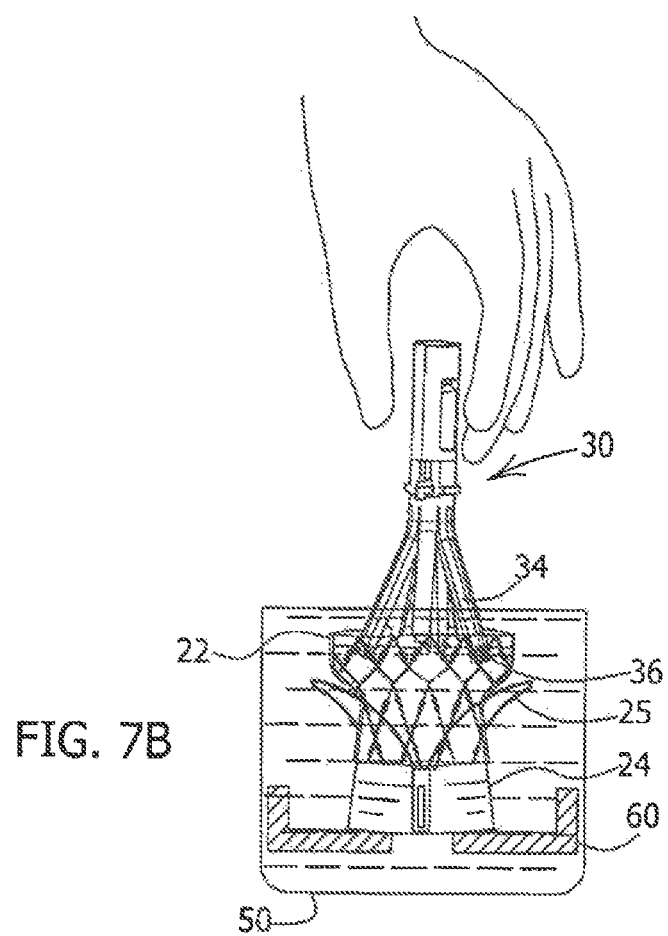
FIG. 7B is a partial cross-sectional view of three-prong loading tool attached to the stent-mounted valve of FIG. 7A by the user.

FIGS. 7A and 7B show alternative delivery packaging for the stent-mounted valve (20). In this variation, loading tool (30) and the converging shape crimping tool (48) are provided separately from the stent-mounted valve (20). In this variation, the stent-mounted valve (20) is enclosed in closed packaging, storage container (50) having closure or lid (54). The storage container (54) is typically filled with a liquid, e.g., comprising a preservative such as glutaraldehyde. The exemplified stent mounted valve (20) is shown having stent (22) with strut supports (24). A base (60) may be provided in the storage container (50) for supporting stent-mounted valve (20) in the liquid medium.

The various disclosed devices and combinations are also useful for other types of expandable stents, stent/valve combinations, and expandable prosthetics that are to be collapsed for delivery, delivered via a transcatheter procedure, and expanded at or before delivery.

In the variation shown in FIGS. 7A and 7B, to remove the stent-mounted valve (20) from the packaging, the user first removes cover (54) from storage container (50). The user the grasps loading tool (30) and slightly compresses prongs (34) inward and aligns the notches (36) of prongs (34) with the corresponding stem connectors (26) or regions of stent (22) such that when the prongs (34) are released in a controlled manner, stent (22) becomes connected to loading tool (30), as seen in FIG. 7B.

As noted above, prior to loading into the catheter delivery tube, the stent-mounted valve (20) may be washed to remove the preservative.

FIGS. 8-11 show the operation of the components, particularly the loading tool (30), stent-mounted valve (20), and converging-shape crimping tool (48), as they are taken from the integrated packaging (shown in FIG. 6) and placed in the catheter housing, and as the valve is implanted in the heart.

Figure 8:
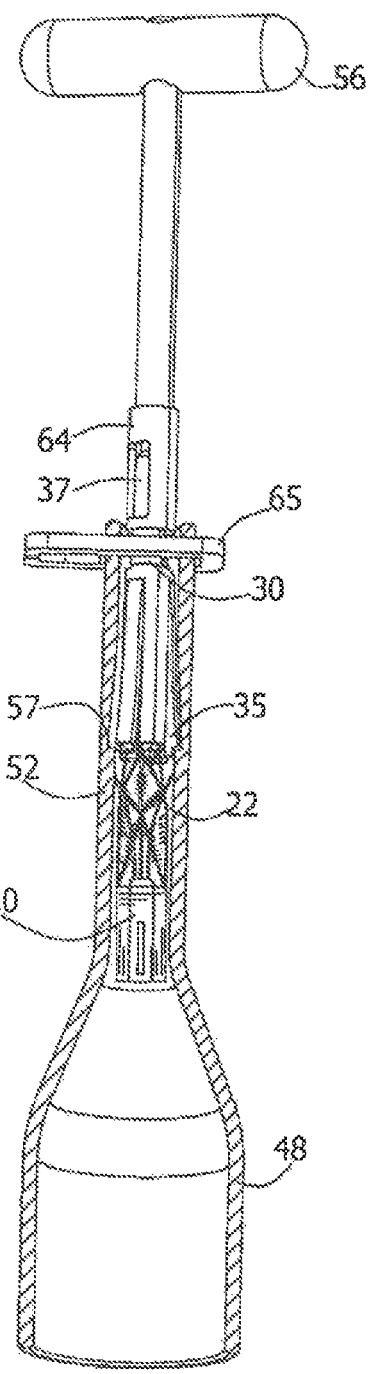
FIG. 8 is a partial cross-sectional view illustrating the loading tool and stent-mounted valve of FIG. 6 after the stent-mounted valve and the loading tool have been crimped inside of the converging-shape crimping tool.

FIG. 8 is a schematic view illustrating the loading tool (30) and stent-mounted valve (20) after they have been removed from the packaging (50) a FIG. 6 and after the stent-mounted valve (20) and the loading tool (30) have been respectively, crimped and collapsed inside of the converging-shape crimping tool (48). The crimping of stent-mounted valve (20) and the collapsing of the prongs (34) of loading tool (30) are accomplished by pulling upwardly on handle (56). Handle (56) draws those components up and through converging-shape crimping tool (48) causing the prongs (34) of loading tool (30) to switch from an open to a closed configuration while remaining connected to stent-mounted valve (20).

Handle (56) is removably attached to loading tool (30) perhaps via a quick-release type mechanical coupling (64). However, other suitable coupler designs may be employed for removably connecting handle (56) to loading tool (30). A two position sliding clasp (65) or stopper is provided on the top of crimping tool (48). The sliding clasp (65) is shaped such that when in a first open position, handle (56) may be pulled upward. When the sliding clasp (65) is slid to a second (or closed) position, the sliding clasp (65) blocks upward movement of handle (56). Thus, following crimping of stent-mounted valve (20) by pulling it up into the neck (52) of crimping tool (48), the user slides sliding clasp (65) to the closed position and so prevents stent-mounted valve (20) and loading tool (30) from being prematurely released from crimping tool (48).

FIG. 8 also shows a circumferential indentation (57) in neck (52). This indentation (57) serves as a "safety stop," in the sense that it prevents the stent-mounted valve (20) from retracting into the larger diameter section a the crimping tool (48) after it has been pulled into the narrow neck (52). Specifically, as loading tool (30) and stent-mounted valve (20) are drawn upward through crimping tool (48), short prongs (35) of loading tool (30) engage indentation (57). This serves to prevent the stent mounted valve (20) from descending into the crimping tool (48), particularly after the handle (56) is removed, and to thereby prevent unwanted re-opening of stent-mounted valve (20). In sum, sliding clasp (65) prevents upward movement of loading tool (30) and valve (20); indentation (57) and short prongs (35) prevent downward movement of loading tool (30) and valve (20).

Figure 9:
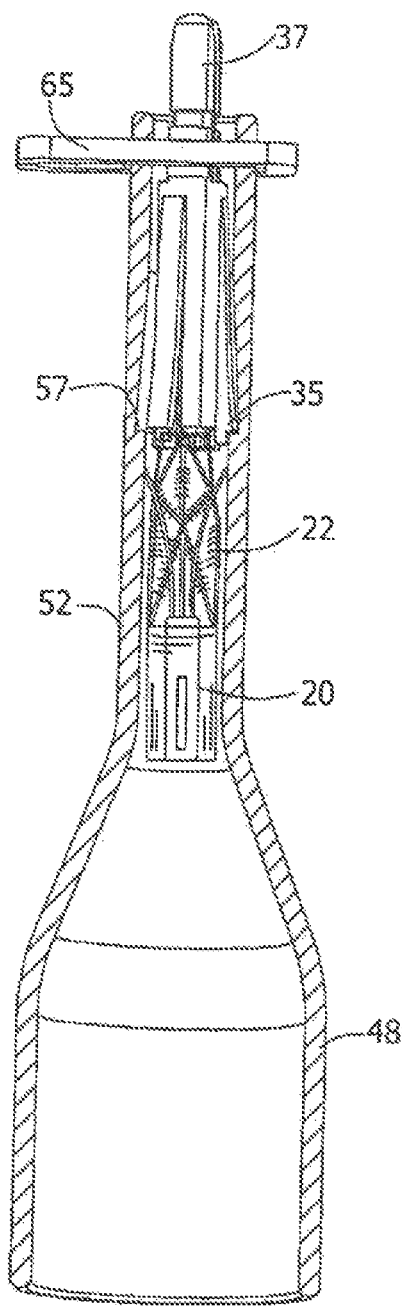
FIG. 9 is a partial cross-sectional view illustrating the loading tool and stent-mounted valve of FIG. 6 after the handle has been detached from the top of the loading tool.

As is shown in FIG. 9, handle (56) is detached from loading tool (30) following crimping of stent-mounted valve (20) and loading tool (30) and subsequent closing of sliding clasp (65).

Figure 10:
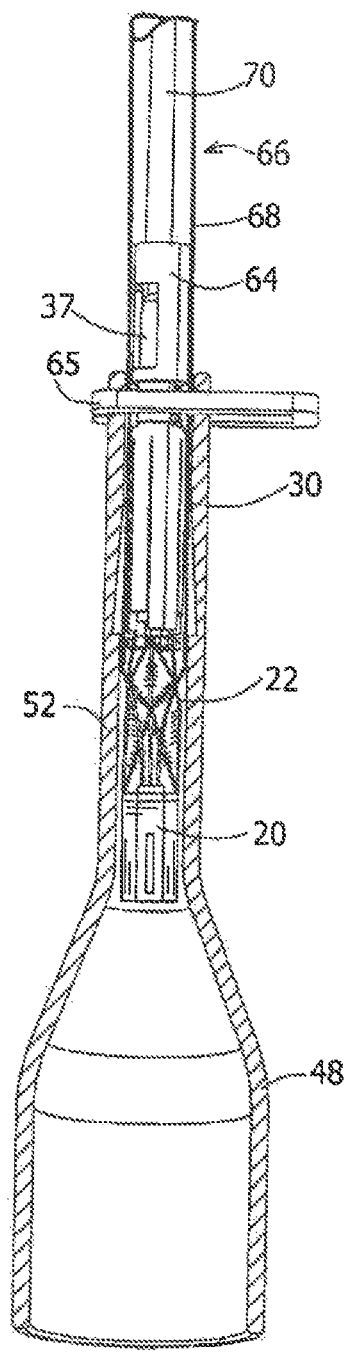
FIG. 10 is a partial cross-sectional view illustrating the loading tool and stent-mounted valve of FIG. 6, after the catheter has been attached to the sipper end of loading tool.

As illustrated in FIG. 10, loading tool (30) is then attached to a delivery catheter (66), comprising a catheter delivery tube (68) and an inner shaft (70) that extends coaxially through the interior a catheter delivery tube (68) to the loading tool (30). A mechanical coupling (64) connects the pusher or base connector (37) of loading tool (30) to inner shaft (70) of delivery catheter (66). Inner shaft (70) has the dual function of pulling the loading tool (30)/valve (20) into the catheter tube (68) and pushing the valve (20) our of the catheter tube (68) at implantation due to the relative motion between the inner shaft and the delivery tube. Said another way: backward movement of shaft (70) relative to the catheter delivery tube (68) causes loading tool (30) and stent-mounted valve (20) to be drawn out of crimping tool (48) and into catheter delivery tube (68). The loading tool (30) and stent-mounted valve (20) remain crimped or collapsed after entering the catheter delivery tube (68). The crimping tool (48) is then released and may be discarded. At this juncture, loading tool (30) and stent-mounted valve (20) are then retracted further into delivery catheter (66) by shaft (70). The assembly is then ready for passage through another catheter (or "outer tube") to the implantation site in the heart.

Figure 11:
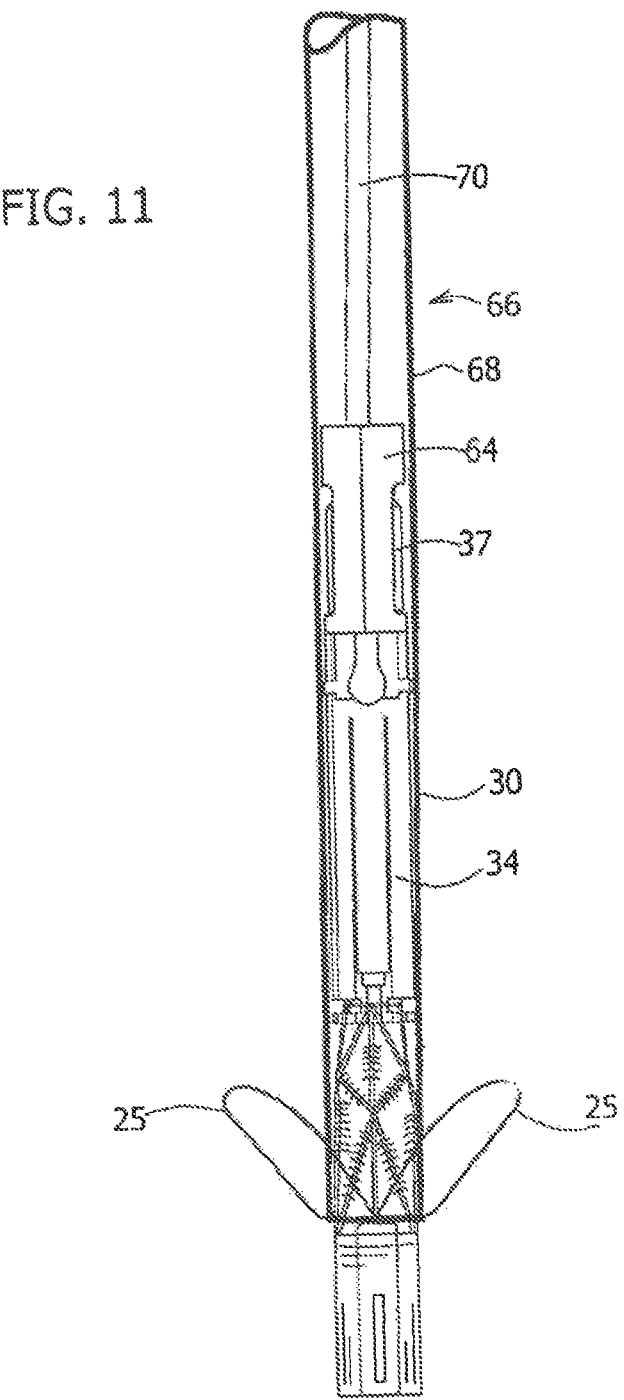
FIG. 11 is a side view illustrating the loading tool and stent-mounted valve of FIG. 6, after the loading tool and valve have been retracted into the catheter delivery tube and the converging-shape crimping tube has been removed.

In FIG. 11, engagement arms (25) are shown to be external to catheter tube (68) during the passage of the stent-mounted valve (20) to the delivery site. During implantation, the delivery catheter (66) is advanced over a guidewire until the distal tip of the stent-mounted valve (20) and the engagement arms (25) pass through the native aortic valve. The delivery catheter (66) is then slightly withdrawn to flare the engagement arms (25) laterally into the valve sinuses. At this point, the stent is still in a compressed state in the catheter delivery tube (68).

Figure 12:
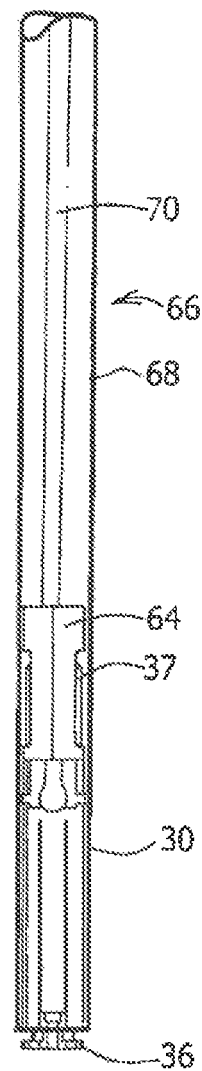
FIG. 12 is a schematic view illustrating the loading tool and the stent-mounted valve of FIG. 6, after the stent-mounted valve has been released from the catheter delivery tube during the implantation procedure.
Figure 12:
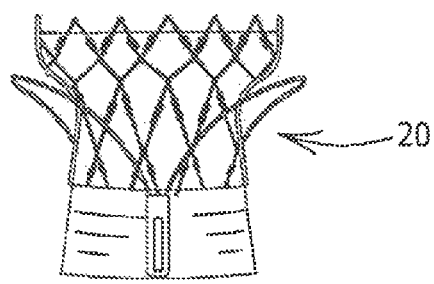

Subsequent retraction of the catheter delivery tube (68), while maintaining the stent-mounted valve (20) stationary using the inner shaft (70), causes release of stent-mounted valve (20) and its placement and opening within the native heart valve orifice. The releasing and opening of the stent-mounted valve (20) causes the stent (22) to expand away from and be automatically disconnected from the still-compressed loading tool (30), as seen in FIG. 12. As mentioned above, the prongs (34) of the loading tool (30) reside in the interior of the stent (22), and when the stent (22) opens, the stent connectors readily exit the notches (36) formed in the prongs (34) of the loading tool (30).

Having described the invention with regard to certain specific embodiments thereof, it is to be understood that the description is not meant as a limitation, since further modifications may now suggest themselves to those skilled is the art, and it is intended to cover such modifications as fall within the scope of the appended claims.

We claim:

1. A loading system for loading a valve prosthesis into a delivery catheter, the loading system comprising:
    a loading tool comprising a loading tool connection member, wherein the loading tool connection member comprises a first plurality of prongs, wherein the loading tool connection member includes an open state with the first plurality of prongs flared outwardly and a closed state with the first plurality of prongs radially contracted;
    a valve prosthesis including a radially compressed configuration and a radially expanded configuration, the valve prosthesis comprising valve prosthesis connection members configured to removably engage with a respective one of the first plurality of prongs, wherein the loading tool is configured to engage the valve prosthesis with the valve prosthesis in the radially expanded configuration and the loading tool in the open state; and
    a crimping tool comprising a proximal end and a distal end, wherein the diameter of the distal end is greater than the diameter of the proximal end,
    wherein the loading tool connection member, in the open state while engaged with the valve prosthesis in the radially expanded configuration, is configured to pass through the crimping tool such that the valve prosthesis crimps from the radially expanded configuration to the radially compressed configuration and the loading tool connection member radially contracts from the open state to the closed state.

2. The loading system of claim 1, wherein the loading tool is configured to automatically disengage from the valve prosthesis when the valve prosthesis is unloaded from a delivery catheter.

3. The loading system of claim 1, wherein the loading tool further comprises a pusher connector disposed opposite the loading tool connection member, wherein the pusher connector is configured for attachment to an inner shaft of the delivery catheter.

4. The loading system of claim 3, wherein the loading tool further comprises a detachable handle configured for attachment to the pusher connector during crimping of the valve prosthesis, wherein the detachable handle is configured for detachment from pusher connector after crimping of the valve prosthesis such that the pusher connector can be attached to the inner shaft of the delivery catheter.

5. The loading system of claim 1, further comprising a storage container for the valve prosthesis, wherein the loading tool and the crimping tool are provided separately from the storage container for valve prosthesis.

6. The loading system of claim 1, wherein each of the first plurality of prongs includes a radially outwardly facing notch, and wherein the valve prosthesis connection members are configured to be inserted into a respective radially outwardly facing notch.

7. The loading system of claim 1, wherein each of the first plurality of prongs includes a radially outwardly facing hook member, and wherein the valve prosthesis connection members each includes an aperture such that each outwardly facing hook member of the first plurality of prongs is configured to be inserted into the aperture of a corresponding one of the valve prosthesis connection members.

8. The loading system of claim 1, wherein the loading tool comprises a second plurality of prongs that are shorter than the first plurality of prongs, each prong of the second plurality of prongs being disposed circumferentially between a pair of prongs of the first plurality of prongs.

9. The loading system of claim 8, wherein the proximal end of the crimping tool includes an inner surface including an indentation, and wherein the indentation is configured to interact with at least one of the second plurality of prongs to prevent the loading tool from advancing distally through the crimping tool after the at least one of the second plurality of prongs is advanced proximally through the crimping tool such that the at least one of the second plurality of prongs is proximal of the indentation.

10. The loading system of claim 1, wherein the proximal end of the crimping tool includes an inner surface including an indentation, and wherein the indentation is configured to interact with at least one of the first plurality of prongs to prevent the loading tool from advancing distally through the crimping tool after the at least one of the first plurality of prongs is advanced proximally through the crimping tool such that the at least one of the first plurality of prongs is proximal of the indentation.

11. A kit comprising:
    a loading tool comprising a loading tool connection member, wherein the loading tool connection member comprises a first plurality of prongs, wherein the loading tool connection member includes an open state with the first plurality of prongs flared outwardly and a closed state with the first plurality of prongs radially contracted;

a valve prosthesis including a radially compressed configuration and a radially expanded configuration, the valve prosthesis comprising valve prosthesis connection members configured to removably engage with a respective one of the first plurality of prongs, wherein the loading tool is configured to engage the valve prosthesis with the valve prosthesis in the radially expanded configuration and the loading tool in the open state;

a crimping tool comprising a proximal end and a distal end, wherein the diameter of the distal end is greater than the diameter of the proximal end; and an openable container surrounding the valve prosthesis, the loading tool, and the crimping tool;

wherein the loading tool connection member, in the open state while engaged with the valve prosthesis in the radially expanded configuration, is configured to pass through the crimping tool such that the valve prosthesis crimps from the radially expanded configuration to the radially compressed configuration and the loading tool connection member radially contracts from the open state to the closed state.

12. The kit of claim 11, wherein the loading tool is configured to automatically disengage from the valve prosthesis when the valve prosthesis is unloaded from a delivery catheter.

13. The kit of claim 11, wherein the loading tool further comprises a pusher connector disposed opposite the loading tool connection member, wherein the pusher connector is configured for attachment to an inner shaft of a delivery catheter.

14. The kit of claim 13, wherein the loading tool further comprises a detachable handle configured for attachment to the pusher connector during crimping of the valve prosthesis, wherein the detachable handle is configured for detachment from pusher connector after crimping of the valve prosthesis such that the pusher connector can be attached to the inner shaft of the delivery catheter.

15. The kit of claim 11, wherein each of the first plurality of prongs includes a radially outwardly facing notch, and wherein the valve prosthesis connection members are configured to be inserted into a respective radially outwardly facing notch.

16. The kit of claim 11, wherein each of the first plurality of prongs includes a radially outwardly facing hook member, and wherein the valve prosthesis connection members each includes an aperture such that each outwardly facing hook member of the first plurality of prongs is configured to be inserted the aperture of a corresponding one of the valve prosthesis connection members.

17. The kit of claim 11, wherein the loading tool comprises a second plurality of prongs that are shorter than the first plurality of prongs, each prong of the second plurality of prongs being disposed circumferentially between a pair of prongs of the first plurality of prongs.

18. The loading system of claim 17, wherein the proximal end of the crimping tool includes an inner surface including an indentation, and wherein the indentation is configured to interact with at least one of the second plurality of prongs to prevent the loading tool from advancing distally through the crimping tool after the at least one of the second plurality of prongs is advanced proximally through the crimping tool such that the at least one of the second plurality of prongs is proximal of the indentation.

* * * * *